United States Patent [19]
Richter

[11] Patent Number: 5,603,326
[45] Date of Patent: Feb. 18, 1997

[54] METHOD AND APPARATUS FOR DISPLAYING AN IMAGE OBTAINED BY ECHO SIGNALS

[75] Inventor: Kari Richter, Berlin, Germany

[73] Assignee: Siemens Aktiengesellschaft, Munich, Germany

[21] Appl. No.: 525,774

[22] PCT Filed: Mar. 18, 1994

[86] PCT No.: PCT/DE94/00303

§ 371 Date: Sep. 20, 1995

§ 102(e) Date: Sep. 20, 1995

[87] PCT Pub. No.: WO94/22374

PCT Pub. Date: Oct. 13, 1994

[30] Foreign Application Priority Data

Mar. 22, 1993 [DE] Germany .......................... 43 09 596.8

[51] Int. Cl.$^6$ ...................................................... A61B 8/00
[52] U.S. Cl. .................. 128/660.07; 128/661.02; 128/916
[58] Field of Search .................. 128/660.01, 660.06, 128/660.07, 661.03, 661.04; 73/597, 599

[56] References Cited

U.S. PATENT DOCUMENTS 4,509,368  4/1985  Whiting et al. ........................... 73/624
4,680,966  7/1987  Nicolas ..................................... 73/597

FOREIGN PATENT DOCUMENTS 4037387  5/1992  Germany .

OTHER PUBLICATIONS

Soetano, K. et al. "An In–Vivo Technique for Estimation . . . Using Ultrasonic Tomogram", Jap. Jrnl. of Appl. Phys vol. 24 #1 1985 pp. 84–86.

Nicolas, J. Metal, "Apparatus for Examination of Objects by Ultrasound Echography", EP 0164808 publ. Dec. 1985.

Kossoff, G. et al., "Apparatus for UTS Examination of Deflatable Objects", PCT Publ. No. WO83/02053 publ. 23 Jun. 1983.

Wild, J. J. et al., "Echo Visualization of Lesions of . . . Breast", Cancer Research vol. 14 (1954) pp. 277–283.

Hoyohawa, Y. et al, "Mass Screening of Breast Cancer by UTS Transmission Technique — Theoret. Consid," vol. 24 No. 24–1 (1985) Jap. Jrnl Appl Phys pp. 82–83.

Primary Examiner—Francis Jaworski
Attorney, Agent, or Firm—Hill, Steadman & Simpson

[57] ABSTRACT

In a method for imaging display of a spatially fixed subject with a primary (wave) radiation directed onto the subject, particularly ultrasound, whereby the imaging display ensues with the echo signals received by an echo signal receiver on the basis of the transit time and/or amplitude thereof with reference to a subject axis directed in the spatial direction of the primary radiation, the subject is located between the primary radiation transmitter/echo signal receiver and a reference surface aligned perpendicular to the spatial direction of the primary radiation and that reflects the primary radiation as an echo signal more strongly than other regions of the subject situated in the field of presentation. The average or expected transit time and/or amplitude of an echo signal of primary radiation passing through the subject that is reflected from the reference surface and received by the primary radiation transmitter/echo signal receiver is calculated or predetermined as reference echo signal. The transit time and/or amplitude of an echo signal of the primary radiation passing through the subject reflected from the reference surface and received by the primary radiation transmitter/echo signal receiver is calculated. The deviation of echo signal reflected by the reference surface compared to the reference signal is evaluated.

22 Claims, 6 Drawing Sheets

METHOD AND APPARATUS FOR DISPLAYING AN IMAGE OBTAINED BY ECHO SIGNALS

BACKGROUND OF THE INVENTION

1. Field of the Invention

The present invention is directed to a method and to an apparatus for this method of displaying an image wherein the signals forming the image are obtained by irradiating an examination subject with a radiation field, such as ultrasound, and detecting the reflected (echo) signals.

2. Description of the Prior Art

A precautionary examination of the female mammary gland for early detection of breast cancer with imaging methods is extremely desirable since this illness, which represents the most common type of cancer in women in industrialized countries, has a significant tendency to spread and an early detection of the sickness usually means a cure.

By contrast to x-ray mammographic examinations, ultrasound examinations are completely non-hazardous and even extremely dense gland tissue (mastopathy) does not represent a problem since the tumors in dense gland tissue can be visibly identified in a sonographic display. X-ray mammography provides no diagnostic utility given patients with a mastopathy or with endoprotheses in the breast region since the tumors can then not be displayed or can only be poorly displayed.

By contrast thereto, however, many previous sonographic methods were incapable of exceeding x-ray mammography in the early detection of malignant tumors in the case of breast examination with respect to sensitivity and specificity. It is precisely this capability, however, that would be desirable since an ultrasound method would represent the ideal examination method because of the completely risk-free nature thereof.

An ultrasound examination is normally undertaken with an acoustic head (applicator) that the physician places onto the organ to be examined in order to thus acquire a tomogram which, as a so-called B-image, corresponds to a slice presentation. Methods are also known that superimpose a number of images registered from different directions on one another in the fashion of a computer tomograph.

A method and an apparatus for producing an image from ultrasound echoes is known from the article by K. Soetanto, "An in-vivo technique for estimation of size and relative sound velocity of breast tumor using distorted image in ultra-sonic tomogram", which appeared in Japanese Journal of Applied Physics, Vol. 24, No. 24-1, 1985, Tokyo (JP), pp.84–86. This describes a method for estimating the size and relative speed of sound in a breast tumor wherein a distorted ultrasound image is evaluated. The distortions arise because tumorous tissue has a different speed of sound than healthy tissue. The article describes investigations of a cylindrical member situated in a water tank, this member having a speed of sound therein different from the surrounding water and a reflector plate arranged therebehind. A linear distortion of the ultrasound image of the reflector plate arises because of, the different speeds of sound and the reflector plate in the ultrasound image has lateral tails because of, the refraction of the ultrasound waves is visible in the ultrasound image. The spacing of the tails from one another indicates the diameter of the cylinder. This perception is then used in ultrasound echo tomography of the female breast. The chest wall behind the tumor is used as the planar reflector. The ultrasound examination itself is implemented with a normal ultrasound apparatus, whereby the examining person can freely move the ultrasound transducer without auxiliaries.

In an ultrasound tomography apparatus disclosed by U.S. Pat. No. 4,509,368, transmitted and reflected signals are superimposed and correlated. Although this arrangement enables a gain in information compared to previously known solutions, systems operating according to this method have not been used in practice in significant numbers. It is thereby an impediment that the apparatus is relatively complicated in structure and that a plurality of acoustic transmitters and acoustic receivers are required, as a result of which the apparatus is expensive to acquire and is also not simple in terms of manipulation.

Further, German OS 40 37 387 discloses a method wherein the echo values obtained for coinciding spatial points from radiation directions opposite one another are superimposed, so that signal parts ultimately remain only for those spatial points that deviate from one another dependent on the radiation direction. As a result, information with respect to the shape and the surface structure of a recognized inhomogeneity can be derived better, since acoustic occlusions and the like are eliminated. It is still a disadvantage of this method, however, that the part of the body to be examined must be irradiated from two opposite spatial directions, so that the acoustic head must either be shifted correspondingly in location or two acoustic heads are required.

Published PCT Application 83/02053 also discloses an ultrasound scanner means for producing ultrasound tomograms of the female breast. The breast is thereby situated in an examination position that corresponds to the examination position in X-ray mammography, so that the ultrasound mammogram can be easily correlated with the X-ray image. The ultrasound scanner means includes an ultrasound-transmissive plate on which the breast is seated. A movable ultrasound transducer or an ultrasound array with which a complete scanning of the breast can be implemented is situated under the plate. Similar to X-ray mammography, an external compression with an air-filled or water-filled balloon or with sand bags or vacuum means as well can ensue. The means needed for compression, however, impede access in the upper breast region. It is noted with respect thereto in the reference that this region should remain free so that it can be brought into a shape wherein the visibility of details is optimized.

SUMMARY OF THE INVENTION

It is an object of the present invention to provide a method and an apparatus for producing an ultrasound image from received ultrasound echo signals wherein the information derivable from the ultrasound image in ultrasound examinations, particularly in serial examinations within the framework of cancer prevention (screening), has particular diagnostic capability.

The above object is achieved in a method and apparatus for producing an image of a portion of the human body with echo signals of primary radiation directed at the portion of the human body, wherein the body portion is disposed between a primary radiation transmitter/echo signal receiver and a reference surface which reflects the primary radiation as an echo signal more strongly than other regions of the body portion situated in the field view of the radiation transmitter. The average or expected transit time and/or amplitude of an echo signal of the primary radiation passing through the body portion, that is reflected from the reference surface and received by the receiver, is calculated, or is set to a predetermined value, as a reference echo signal. The actual transit time and/or actual amplitude of an echo signal of the primary radiation passing through the body portion and reflected from the surface and received by the primary radiation receiver is calculated. The deviation of the transit time and/or amplitude from the actual echo signal reflected from the reference surface compared to the reference echo signal is evaluated, and this deviation is used as a criterion for the probability of a tumor in the region of the direction of propagation of the received echo signal. The reference surface is aligned perpendicularly to the primary propagation direction of the primary radiation, and the body portion is clamped, so as to be spatially fixed in position, between a plate-shaped clamping element and the reference surface, the plate-shaped element and the reference surface being substantially parallel.

The invention is based on the perception that influence of a malignant tumor on the transit time and/or amplitude of an ultrasound signal reflected by the malignant tumor deviates from the influence on transit time and/or, amplitude of a reference ultrasound signal transmitted by healthy tissue. Thus a reference signal is generated by arranging an object at the far side of the part of the body to be examined, the object being highly ultrasound-reflective and spatially fixed at a predetermined distance from the transmitter/receiver. The reference signal enables an evaluation of the influencing of the transit time and/or of the amplitude change. The deviation in transit time and/or amplitude of received echo signals compared to the known or identifiable transit time of the reference echo signal and intensity of the reference echo signal registered as amplitude, is then, taking the registered amplitude curves into consideration, used as a criterion for the tumor probability in the area of the spatial direction of the propagation of the respective echo signals. The change in transit time thereby results from the respectively different, resultant propagation speed of the sound in different tissue areas, whereas acoustic cancellation (or amplification) is produced by diffraction and reflection phenomena.

The apparent position and displayed intensity of a reference surface that is arranged at the other side of the part of the body to be examined and is aligned perpendicularly to the spatial direction of the emitted ultrasound signal is thereby distorted and shifted in the regions beyond a tumor which causes the image of the reference surface to be displayed to be modified from an expected position or appearance. Conclusions about the probability of a tumor in the area of the part of the body above the shift can be drawn on the basis of the arrangement, the nature of the edge contour and the amount (or the direction) of the shift.

An important feature of the inventive method and apparatus is that a linking or correlation of picture elements of the image containing only two-dimensional information (and thus corresponding to pixels as are required by shadowing as in fluoroscopy) with depth information obtained from the echo signal, so as to obtain three-dimensional information. The inventive ultrasound method and apparatus thereby enable depth locating of findings that are emphasized or can only be initially localized with the inventive, two-dimensionally imaging method steps.

For calculating the transit time of the echo signal, the echo signals that have an amplitude upwardly exceeding a predetermined level within a defined time window are registered by the ultrasound transmitter/receiver in an embodiment of the inventive method. The level is dependent on the nature of the reference surface employed and the time window is located in the region of the echo signal in which one can count on a transit time shift of the relative exultation of the amplitude level deriving from the reference surface. Either the absolute or, on the other hand, only the relative transit time deviation can thus be calculated in the region of the time window. A calculation of the transit time deviation in the region of the time window prevents other, acoustically reflective regions of the body part under examination such as gland members, fatty tissue, etc., generating a similar amplitude from being erroneously confused with the reference surface.

In general form, regions of the image presentation can thereby be generated by common evaluation of echoes registered for points neighboring one another, so that a complete display of the reference plane is enabled given maximum utilization of the registered signal information.

The points or regions can be superimposed to form a two-dimensional or three-dimensional graphic display, particularly a color display.

The inventive method can also be employed for a spatial image presentation in the fashion of computer tomography by emitting primary radiation onto the body part to be examined along a path covering the area of the body part either continuously or in an essentially equidistant succession of adjoining spatial directions (i.e., a number of slices).

An embodiment of an apparatus for the implementation of the inventive method thus includes the corresponding radiation sources or and radiation receivers forming signal transducers as well as a signal processor with a program memory and signal connections to the signal transducers.

Since the wave radiation scans the relevant body part, i.e. the subject to be examined, in chronological succession and a stable support of, in particular, moving subjects is beneficial in this respect, the subject in the preferred embodiment of the inventive apparatus is arranged between a plate-shaped element that is essentially transparent for the wave radiation and the reference surface that reflects the echo signals, whereby the element and the reference surface are aligned parallel to one another.

Because subjects to be examined can have different shapes, the element transparent for the wave radiation and the reflective reference surface are connected to one another with an axial adjustment means. The subject to be examined and surrounded by a coupling medium is thus clamped in a fixed fashion by actuating the adjustment means after introducing the subject between the reference surface and the element, which are likewise provided with the coupling medium, so that relatively large regions of the subject directly touch the element and the reference surface and a good coupling between subject and the element and the reference surface is thus guaranteed in a simple way. Since the thicknesses of the regions to be traversed by the ultrasound signal are thus defined, a transmitter/receiver having suitable focusing can be selected, so that losses in time due to mismeasurements are avoided.

The coupling medium surrounding the subject is preferably confined in a flexible container whose shape can be adapted to the shape of the subject. The container is made of a material transmissive for the wave radiation and the coupling medium is such that the speed of sound and/or the absorption of the wave radiation in the coupling medium is essentially the same as that of the wave radiation in the body tissue of the subject to be examined. As a result, those regions of the subject whose surface does not reside in immediate contact with the transmissive element or the reflective reference surface can also be examined.

In a preferred embodiment of the inventive apparatus, the ultrasound transmitter/receiver can be locked in a carriage lying against the outside surface of the plate-shaped element transmissive for the wave radiation and arranged translationally movable such that the subject to be examined together with the reflective reference surface behind it can be scanned grid-like point-by-point in chronological succession in a simple way either manually or under motor drive. In the case of a linear or two-dimensional array, the required motion sequences are simplified or can be entirely eliminated. In a two-dimensional array embodiment, this itself can form the pressing surface. The drive thereby ensues in scanning fashion with a corresponding electronic circuit.

In the examination of a human body part, the regions of the respective surfaces of the element transmissive for the wave radiation and the reflective reference surface are matched to the shape of the body part adjacent thereto and, in particular, are provided with a connecting edge having a concavely shaped recess. This is a preferred arrangement, in particular, for examining the female mammary gland.

In a preferred embodiment for evaluating the obtained information, a computer-calculated, three-dimensional display of the ultrasound-reflective reference surface is produced on a monitor, so that the size of the region of the subject to be examined wherein a tumor is present with high probability can be simultaneously surveyed. The simultaneous display of the characteristic information is thus possible in a single image that can be aligned in different views by the corresponding, graphic control means of the computer.

A closer diagnosis can then ensue by selecting the display of the tissue regions associated with the conspicuous regions of the reference surface. By enlargement (zoom) of an image excerpt, tissue zones of interest can thereby be separately reproduced, so that a more exact evaluation is possible.

DESCRIPTION OF THE PREFERRED EMBODIMENTS

Figure 1:
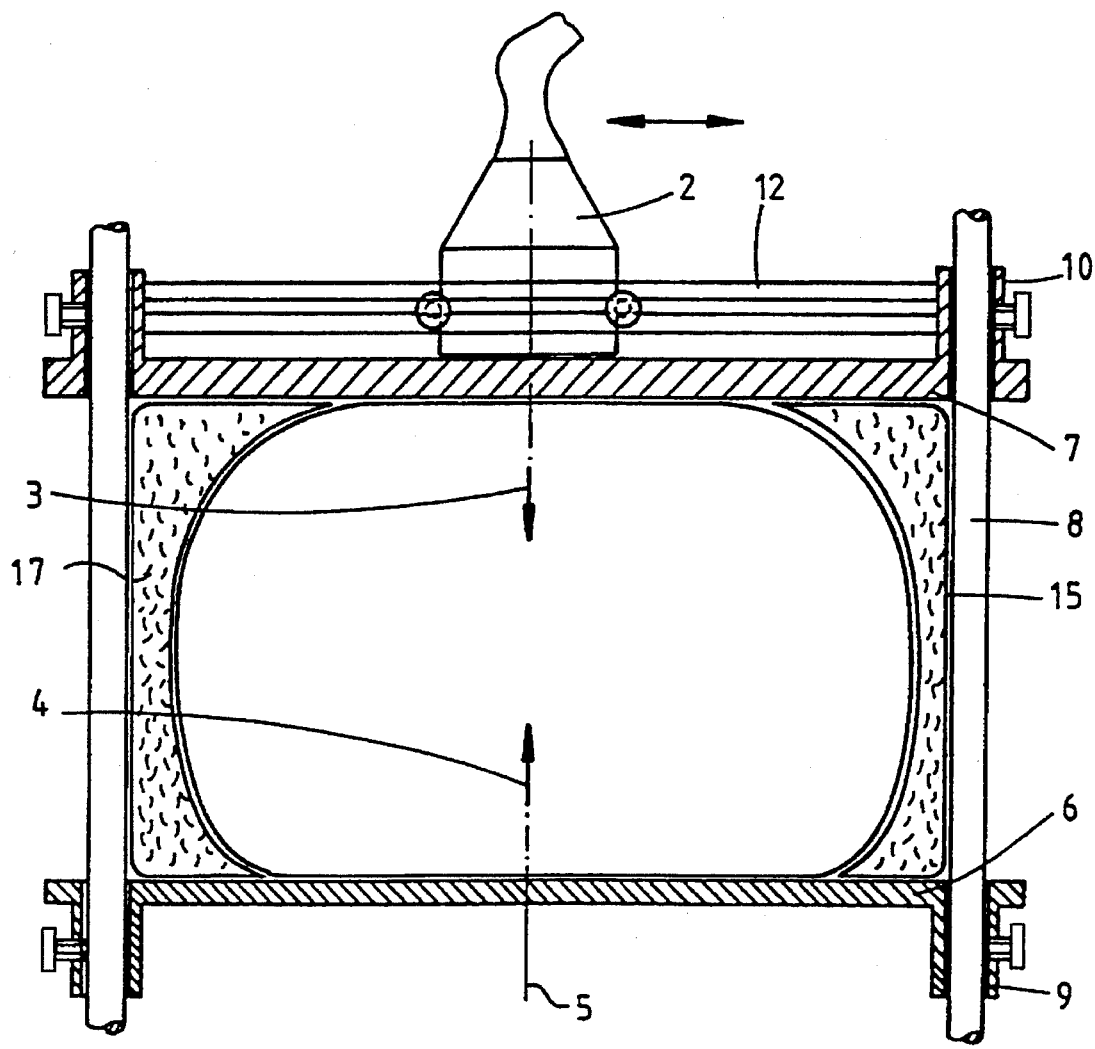
FIG. 1 illustrates the preferred embodiment of the inventive apparatus for the implementation of the inventive method, shown in section.
Figure 1:
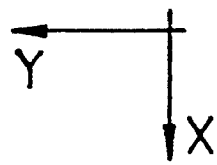
Figure 2:
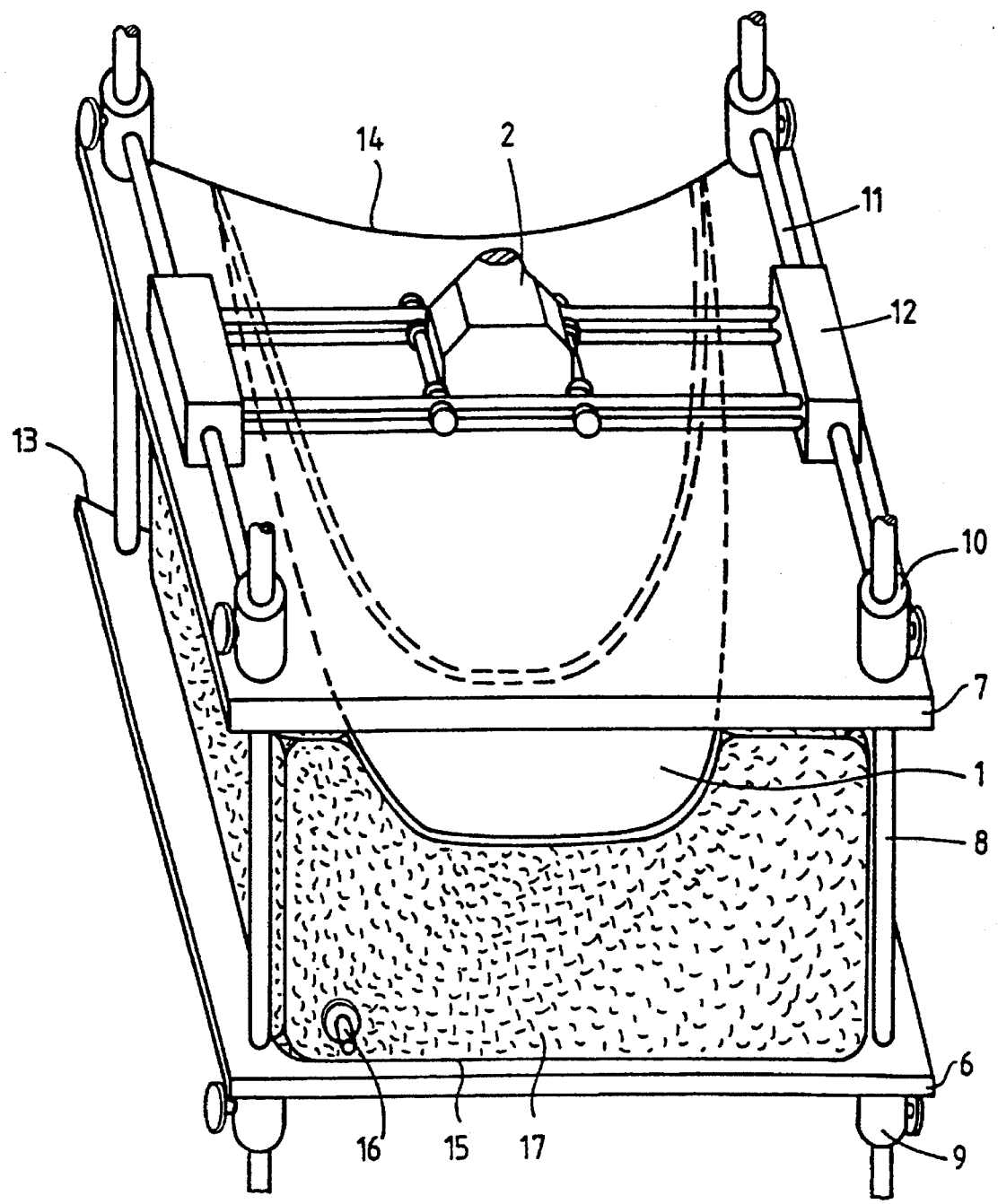
FIG. 2 illustrates the apparatus of FIG. 1 in a perspective view.

In the preferred embodiment of the inventive apparatus shown in FIGS. 1 and 2, two plane-parallel elements, a plate 6 and an element 7, are provided that limit the subject 1 to be examined in two directions in two planes aligned essentially parallel to one another. The element 7 is transmissive for ultrasound waves, whereas the plate 6 reflects ultrasound waves. Plate 6 and element 7 are connected to one another with an axial adjustment mechanism 8. The spacing between the element 7 and the plate 6 can be individually set with adjustment elements 9 and 10. The following spatial directions shall be employed for the following description: x forms the penetration direction of the ultrasound signals and, thus, the t-axis for the ultrasound echoes received in chronological succession. The y-axis forms a first "motion" axis in the signal pick-up and, thus, the second coordinate for the illustration of a tomogram. The z-axis then forms the secondary motion axis of the signal pick-up and thus enables the generation of a three-dimensional image. The "motion", however, need not ensue mechanically but can be undertaken by electronic scanning given the employment of linear or planar transmitter/receiver arrays.

The primary wave transmitter/echo signal receiver 2 is arranged so as to be movable and lockable in a carriage 12 along the longitudinal axis of the carriage 12 that is likewise connected to cross-rods 11 of the adjustment mechanism 8 in this preferred embodiment of the apparatus. The carriage 12 is in turn displaceable along the longitudinal axis of the cross-rods 11. The primary wave transmitter/echo signal receiver 2, which lies against the outside of the element 7, can move over the entire planar surface of the element 7 with the carriage 12 for scanning the subject 1 to be examined. The position, i.e. the spatial direction, of the primary wave transmitter/echo signal receiver 2 can be set either manually or driven by a stepping motor or with electronic scan means. Given manual setting, the coordinates or the position of the primary wave transmitter/echo signal determining the spatial direction are acquired.

The respective edges 13 and 14 of the plate 6 and of the element 7 lying against the human body are anatomically rounded, in particular, concave.

This preferred exemplary embodiment is especially simple in mechanical terms because an examination subject 1 having an arbitrary shape can be surrounded at any time by a flexible, sealed container 15 that contains a coupling medium 17 and is transmissive for the (wave) radiation employed. The container 15 is filled and emptied via a filling nozzle 16. In addition, the coupling medium must merely be applied to the plate 6 and to the element 7 in order to assure that the wave radiations can be well-transmitted.

In a further embodiment of the inventive apparatus that is not shown, the reflective plate 6 simultaneously forms a reception means for a further imaging signal effective in spatial direction.

Such a further examination may be an x-ray examination or a digital radiography examination of the subject in the identical position. Further information with respect to the detected inhomogeneity can thereby be acquired with an advantageous reduction of the x-ray load by comparison examinations conducted only by means of x-ray exposures from two different spatial directions that are currently standard. The x-ray tube can thereby temporarily take the place as warranted of the ultrasound transmission and reception means.

Thereafter, the subject 1 to be examined is fixed with the adjustment mechanism 8 employing the adjustment elements 9 and 10 and the primary radiation signals 3 emitted by the primary wave transmitter/echo signal receiver 2 are reflected by the plate 6, after passing through the subject 1, as echo signals 4, and are picked up by the primary wave transmitter/echo signal receiver 2. The transit times and the amplitudes of the echo signals 4 are thereby registered for the different spatial directions 5 of the emitted primary radiations 3 by the evaluation means connected to the primary wave transmitter/echo signal receiver 2.

The signal curves that arise for the various at boundaries of inhomogeneities and the signal curves therefrom shall now be discussed in greater detail with reference to FIGS. 3a–3d and 4a–4d.

The sectional views according to FIGS. 3a–3d show various inhomogeneities in an examination subject which become apparent upon transirradiation with ultrasound (in the x-direction) for explaining the inventive method. The spatial direction of the primary radiation is in the direction of the arrow, whereby the degree of shading of the illustration indicates the number or the intensity of the echoes obtained.

Figure 3D:
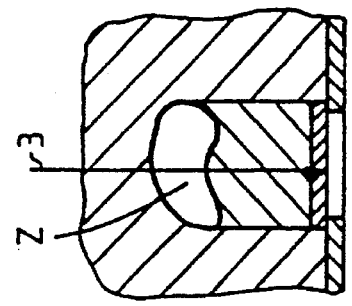
FIGS. 3a–3d schematic views of tissue inhomogeneities shown in section, as arise upon transirradiation of a subject in accordance with the principles of the present invention.
Figure 3C:
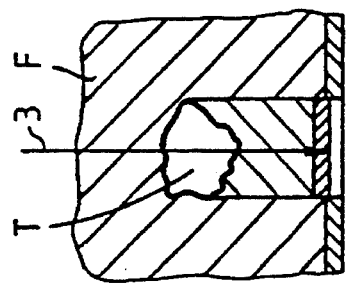
Figure 3B:
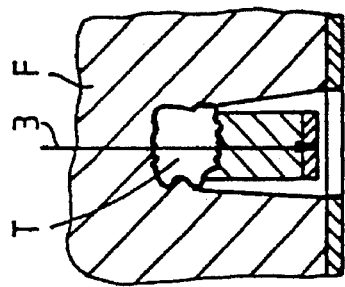
Figure 3A:
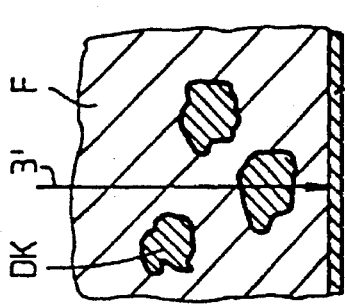

FIG. 3a shows a tumor-free subject containing fatty tissue F and glandular member DK. The fatty tissue F has a lower echo density than the glandular member DK, and the ultrasound-reflective plate P has the highest echo density.

FIG. 3b shows a subject having a malignant tumor T. The malignant tumor appears nearly without echo and with a bilateral edge shadow behind the tumor.

FIG. 3c shows a subject having a malignant tumor T. The malignant tumor appears nearly without echo but, by contrast to FIG. 3b has a moderate central shadow behind the tumor.

FIG. 3d shows a subject having a benign cyst Z. Like most cysts, the cyst Z appears without echoes and with a central sound intensification behind the cyst.

The various echo signal curves respectively arising from FIGS. 3a–3d are shown in FIGS. 4a–4d (z-direction).

Figure 4D:
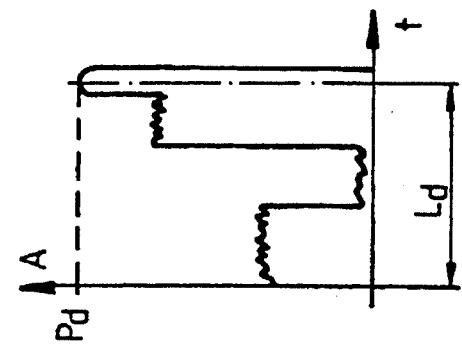
FIGS. 4a–4d show the respective echo signal curves for the views according to FIGS. 3a–3d.
Figure 4C:
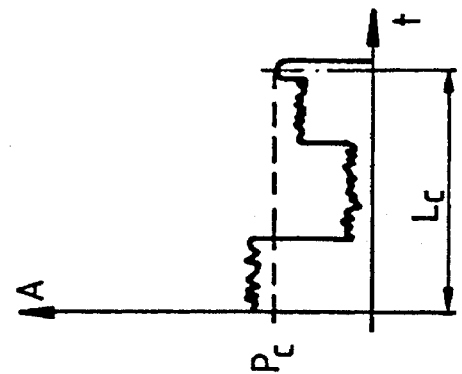
Figure 4B:
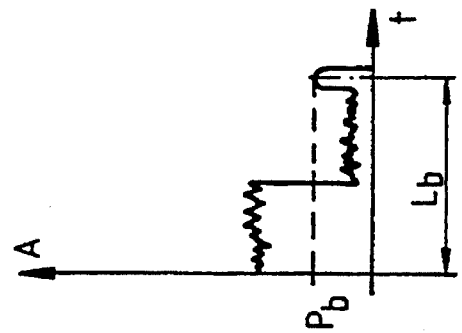
Figure 4A:
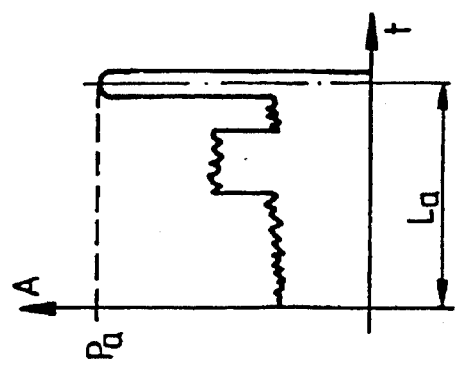

FIG. 4a shows the echo signal curve of the reference primary radiation 3' that passes through the tumor-free subject containing fatty tissue F and glandular member DK. The variations in the echo amplitude A with the time t and, therefore, with increasing distance from the primary radiation transmitter/echo signal receiver are thereby entered. The fatty tissue F has a lower amplitude than the glandular member DK, whereby the region of the highest amplitude values Pa indicates the position of the ultrasound-reflective plate.

FIG. 4b shows the echo signal curve of a primary radiation 3 passing through the malignant tumor T. The amplitude in the region of the tumor T and of the bilateral edge shadow is substantially lower than that of the surrounding fatty tissue F. It may also be seen that the transit time $L_b$ up to the region of the increased amplitude values $P_b$ of the plate has shortened in comparison to the transit time $L_a$ of the echo signal according to FIG. 4a, but the increased amplitude values $P_b$ are lower than the increased amplitude values $P_a$ of the echo signal curve according to FIG. 4a. The shortening of transit time thereby presents itself as an apparent plate deformation.

FIG. 4c shows the echo signal curve of a primary radiation 3 passing through the malignant tumor T. The amplitude in the region of a tumor T is significantly lower than that of the surrounding fatty tissue F and the moderate central shadow has a reduced amplitude compared to the amplitude in front of the tumor T. As can be seen in the same way as in FIG. 4b the transit time $L_c$ up to the region of increased amplitude values $P_c$ of the plate has shortened in comparison to the transit time $L_a$ of the echo signal according to FIG. 4a and, but the increased amplitude values $P_c$ are lower than the increased amplitude values $P_a$ of the echo signal curve according to FIG. 4a.

FIG. 4d shows the echo signal curve of a primary radiation 3 that passes through the benign cyst Z. The amplitude in the region of the cyst Z is essentially equal to zero and the central sound intensification having an amplitude following the cyst Z that is increased compared to the amplitude preceding the cyst Z may be seen. As can also be seen the transit time $L_d$ up to the region of the increased amplitude values $P_d$ of the plate 6 has in fact shortened in comparison to the echo signal curve according to FIG. 4a, but the increased amplitude values $P_d$ essentially continue to exceed the increased amplitude values $P_a$ of the echo signal curve according to FIG. 4a.

By repeated scanning of the subject in further planes directed perpendicularly relative to the first plane, a three-dimensional image can be produced in a further exemplary embodiment (not shown here) via a linking of the identified echo signal curves by superimposition.

FIGS. 5a–5e show five echo signal curves identified at various points in a plane in a selected spatial direction.

Figure 5A:
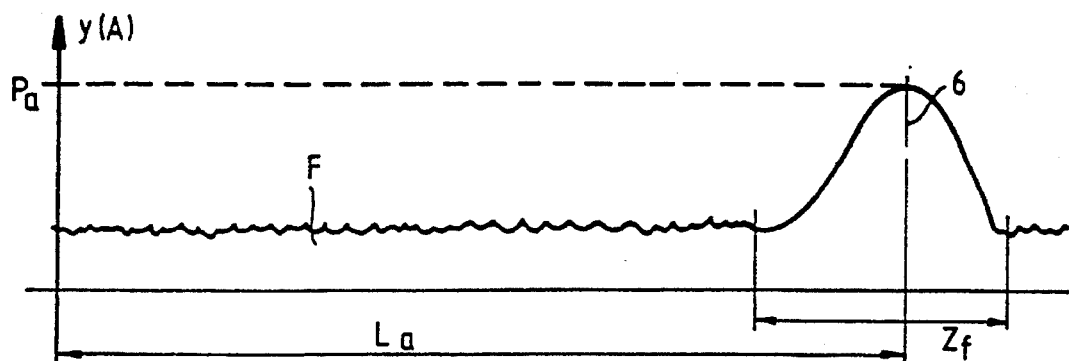
FIGS. 5a–5e illustrate echo signal curves at various registration points of a plane in a selected spatial direction.

According to FIG. 5a, the echo signal passes through fatty tissue F up to the plate 6, in the region whereof the amplitude of the echo signal is substantially boosted relative to the basic level of the amplitude values. The transit time $L_a$ of the echo signal can be calculated with reference to the distance of this region of relatively low amplitude from the zero point of the x-axis (time axis). A time window $Z_f$ can also be defined on the basis of this echo signal wherein one can expect a transit time shift of the relative increase of the amplitude level arising from the plate 6.

Figure 5B:
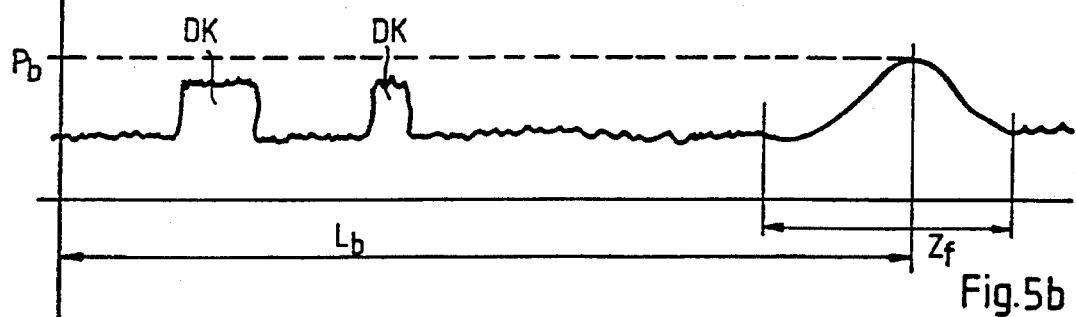

In the graphic illustration of FIG. 5b, the echo signal passes through the subject to be examined in a rastered spacing from the echo signal shown in FIG. 5a and proceeds through two glandular members DK that may be recognized on the basis of the amplitude ranges boosted in the same direction. The transit time $L_b$ of this echo signal thereby corresponds to the transit time $L_a$ of the echo signal of FIG. 5a, so that the position of the relatively increased amplitude value $P_b$ in the time window $Z_f$ corresponds to that of the relatively exalted amplitude value $P_a$ in the time window $Z_f$. The amplitude values for $P_a$ and $P_b$ are thereby essentially alike.

Figure 5C:
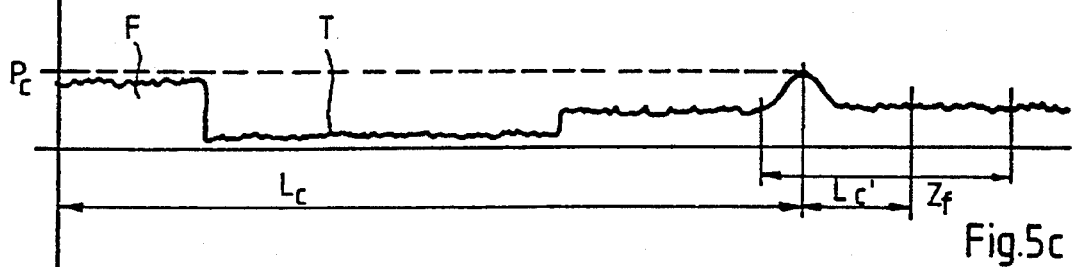

In the illustration of FIG. 5c, the echo signal passes through a malignant tumor T. An extremely low amplitude is registered in the region of the malignant tumor, and the amplitude following the tumor T is lower than preceding the tumor T because of a middle acoustic shadow. The transit time $L_c$ of the echo signal has shortened somewhat by comparison to the echo signals of FIGS. 5a and 5b since the speed of sound in the tumor is higher than in the rest of the body tissue. The relative shortening of transit time within the time window $Z_f$ is shown as $L_{c'}$. The relatively low amplitude value $P_c$ is again located in the time window $Z_f$, but it is now located close to the lower boundary of the time window $Z_f$ because of the shortened transit time $L_c$ and now has a substantially lower value than the relatively low amplitude values $P_a$ and $P_b$ of FIGS. 5a and 5b.

Figure 5D:
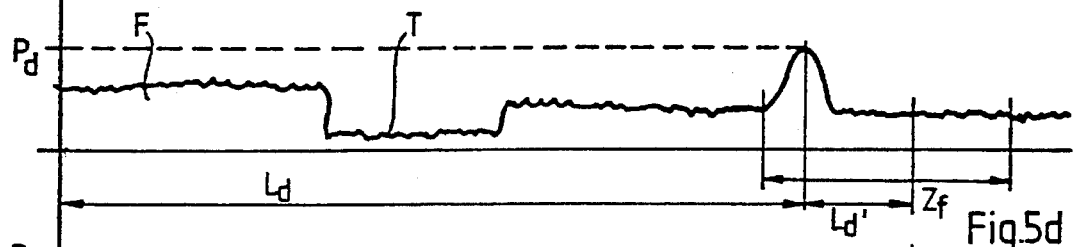

The echo signal according to FIG. 5d also passes through the tumor T but the path of this echo signal through the tumor T is different than that of the echo signal of FIG. 5c, so that, given the same shortening of transit time ($L_d$ corresponds to $L_c$ and the relative shortening of transit time $L_{d'}$ corresponds to $L_{c'}$ within the time window $Z_f$) and position in the time window $Z_f$, the relatively low amplitude value different from the relatively low amplitude value $P_c$ of FIG. 5c.

Figure 5E:
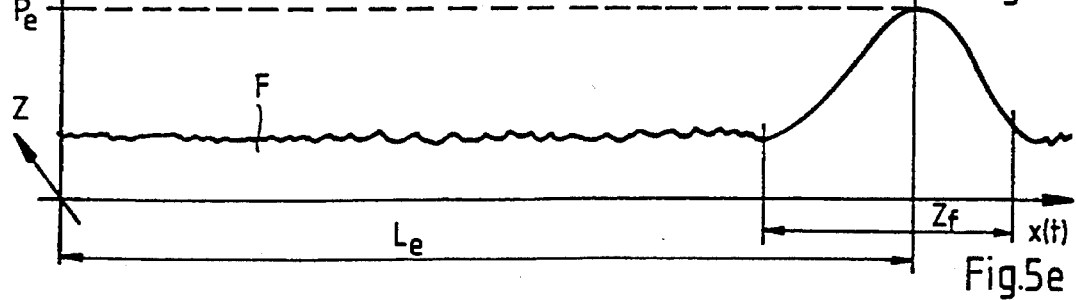

The echo signal shown in FIG. 5e, corresponding to FIG. 5a, again still proceeds through the fatty tissue F, so that a determination can be made on the basis of these five echo signals that a tumor is present in this plane in the region between the points of the emitted primary rays corresponding to FIGS. 5c and 5d, since both shortenings of transit time $L_c$ and $L_d$ or, respectively, the relative transit time shortenings $L_{c'}$ and $L_{d'}$, as well as relatively exhausted amplitude values $P_c$ and $P_d$ were found in the region of the defined time window $Z_f$.

Figure 6:
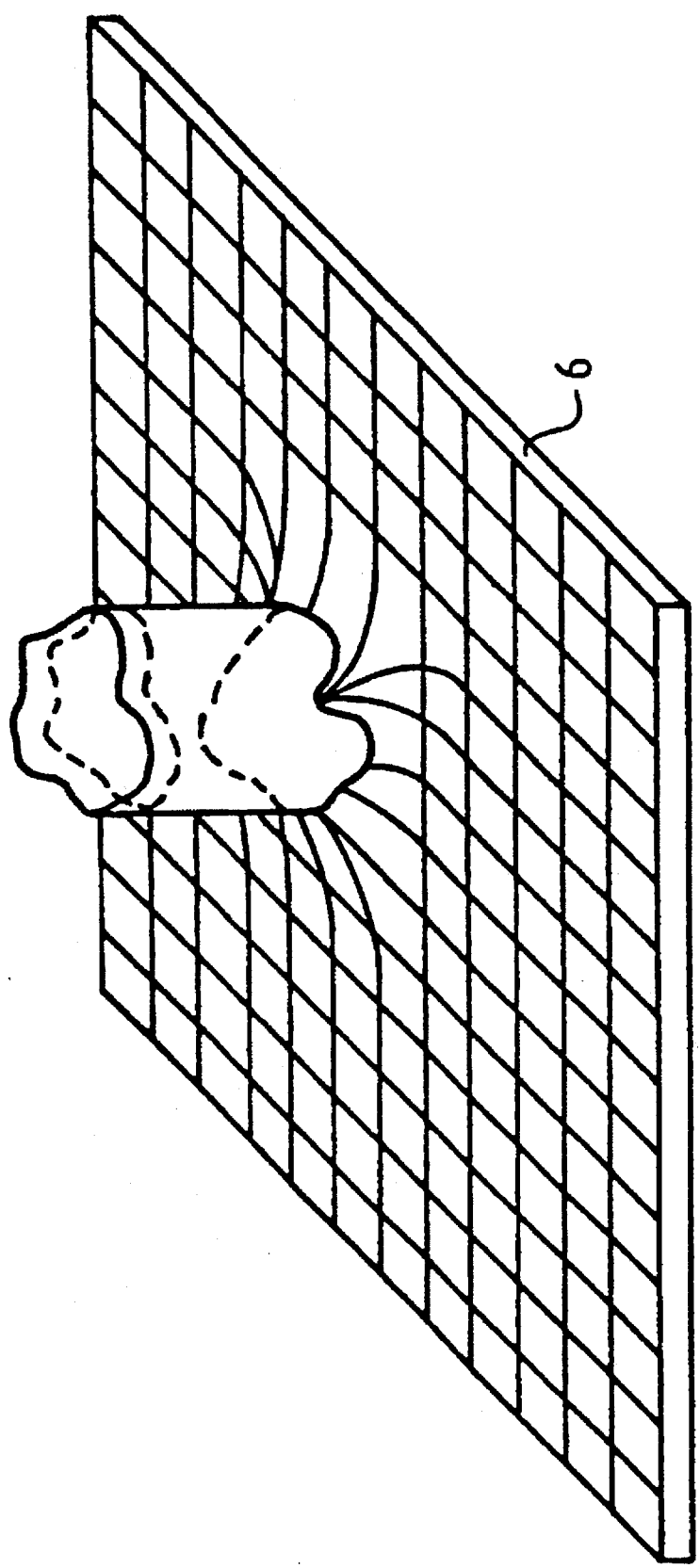
FIG. 6 is a three-dimensional illustration of the ultrasound-reflective support in the ultrasound image given an existing tumor in the subject under examination obtained in accordance with the inventive method and apparatus.

In order to be able to distinguish a benign inhomogeneity that shortens the transit time of the echo signals from a malignant inhomogeneity even better, the resultant ultrasound image of the reflective plate 6 is three-dimensionally shown in FIG. 6. The spatial contour of the region in which an inhomogeneity is to be expected with high probability can thus be graphically reproduced. The nature of the edge contour of the distorted region of the reflective plate 6 can thus be seen, enabling a conclusion about the nature of the edge contour of the inhomogeneity. Studies have shown that malignant findings usually have irregular edge contours. By retrieval of the primary image directed parallel to the direction of acoustic propagation, further, the inhomogeneity causing a disturbance is directly accessible for observation, so that more detailed characterization is possible.

The three-dimensional illustration according to FIG. 6 shows the ultrasound-reflective plate 6 given the presence of a malignant tumor in the subject to be examined. The irregular nature of the contour of the region of the plate 6 displayed distorted can be clearly recognized. It can thus be seen with reference to the nature of the edge contour that there is a high probability of a malignancy being present. Further, a spatially limited region of the body part under examination wherein the malignancy can be expected with high probability can be identified by the projection of the region displayed distorted in the direction of the upper wave-transmissive element.

Figure 7:
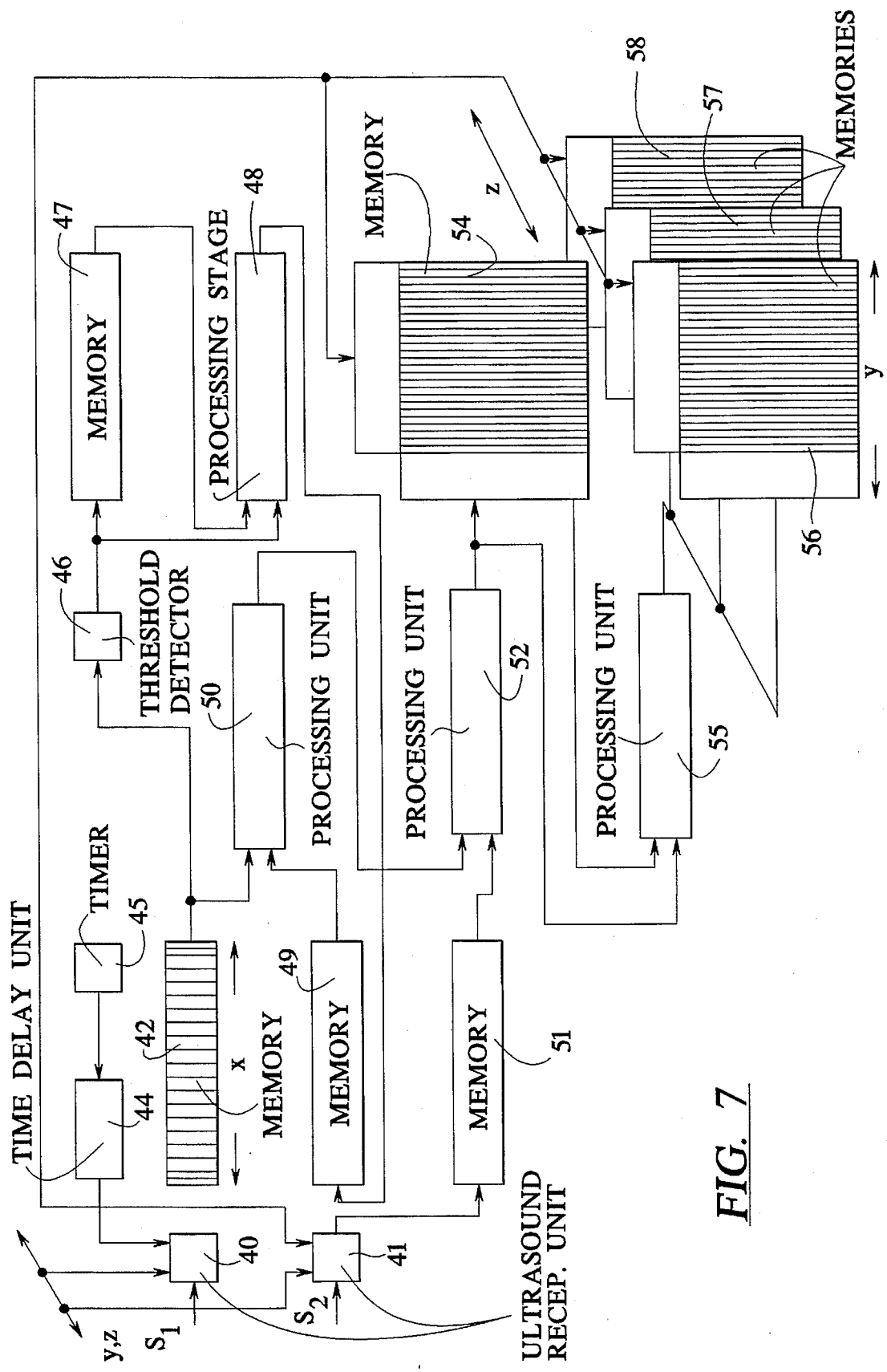
FIG. 7 is a block circuit diagram of a processor system for signal processing in accordance with the inventive method.

Given the fundamental structure of an evaluation means for the inventive method shown in the form of a block circuit diagram in FIG. 7, the ultrasound echoes $S_1$ picked up by an ultrasound reception unit 40 are written into a memory 42 as digitized amplitude signals, for example, into shift registers for the acceptance of the digitized signals. (A further reception unit 41 serves the purpose of receiving another spatially correlated, imaging signal derived from the organ under examination that shall be set forth in greater detail below.) The signal present in the shift register constitutes the digitized amplitude values of the received echo, with reception being started after an output signal of a time delay unit 44 activated by a timer 45 that defines the point in time of emission of the ultrasound signals was activated. The returning signal is thus retained in the memory 42 in response to every ultrasound signal pulse that is emitted, whereby the digitized representation in x-direction (penetration depth) corresponds to that of FIGS. 4 and 5.

The sound reception unit 40 is positioned in different positions with reference to the organ under examination, such as with an apparatus for line-by-line linear shift in the y-direction (see FIG. 3) that is preferably automated. A line-by-line scanning for slice-by-slice presentation of the organ to be examined or the body part to be examined is thus possible. In a modification of the invention (not shown here), the line-by-line scanning can also ensue by simultaneous pick-up of a respective, entire line with a corresponding array of ultrasound transmitters/receivers.

The exemplary embodiment shown in FIG. 7 represents the evaluation circuit for the signals successively registered within a spatial plane, i.e. for a two-dimensional region. An ultrasound transmitter/receiver that emits signals for an entire slice is required for a simultaneous two-dimensional acquisition, whereas such an arrangement would have to be correspondingly multiplied for every further slice to be acquired given a three-dimensional acquisition. This leads to a planar-like array arrangement for the ultrasound transmitters/receivers.

Since, as a consequence of a scanning of the signals registered without mechanical motion, however, the further-processing thereof is ultimately again successively undertaken, the operating mode in the acquisition of the individual, geometric planes is the same, so that processing conforming to the following description ensues.

Upward transgressions of a predetermined threshold in the echo signal that are received and retained in digitized form in the shift register 42 and those that exceed the amplitudes of echoes of body tissue and form echoes of the highly reflective plate are retained with a threshold detector 46. This value is written into an average value or reference value memory 47 wherein the chronological averages of the amplitudes and/or echo delays, or the delay times of the majority of the registered echo delay times of the pulses exceeding the threshold are written. In another version of the illustrated exemplary embodiment, the reference value can alternatively be a permanently prescribed value that is obtained on the basis of empirical values or values that were calculated from the known geometry of the arrangement.

In a further processing stage 48, the difference of the echo time of the registered pulse since the emission thereof, or alternatively its amplitude is calculated compared to the reference value contained in the memory 47 and is forwarded to a memory 49 which stores the shift of the echo of the plate that is "hard" with respect to the reflection properties, or stores the reduction of the echo amplitude due to subject located in the intervening body tissue. This virtual plate deformation or "echo reduction"—as set forth of—forms a further local, characteristic signal for a point of the x, y-plane as an indication for the presence of malignant tissue but without information in the x-direction. The obtained values are retained in the memory 49. In a first processing unit 50, the signal contained in the memory 49 is attached to the output signal of the shift register 42 as further information. This can ensue in a simple way by retaining the value of the echo shift or echo reduction in an additional memory cell provided for that purpose.

A further imaging signal that is characteristic of the corresponding point in the x, y-plane and that is emitted by the signal pick-up 41 and retained in a memory 51 is, as warranted, attached in a second processing unit 52 to the output signal of the first processing stage 50.

This signal is deposited in a memory 54, whereby this memory is organized matrix-like and accepts the entire echo signal (x-axis information) including the aforementioned auxiliary signals for a y-scan line.

In a third processing unit 55, the aggregate signal obtained for a point of the y-axis is now correlated with further signals that were registered at an earlier point in time. These signals are thereby preferably signals adjacent in the z-direction so that conclusions about the tumor probability for a slice of the tissue under observation are obtained from the superimposition of the local depth echo (x-direction), of the local echo shift, the local signal of a further imaging method and the corresponding, neighboring signals in z-direction, this being compared to the current signal or being correlated in some other way. Single modifications compared to neighboring signals can thus also enter into the locally registered signal. Further, correspondingly processed slice images are obtained by further signal pick-up given a shift in the z-direction, the further slice images being deposited in further memories 56–58 (only shown by way of example), so that a three-dimensional image that can be interpreted overall is obtained with the combined content of these memories. The correlation of the contents of neighboring memory locations in the z-direction provides a possibility of improving the obtained information further, as was already shown with reference to the example of the third processing unit 55. Correspondingly, a correlation of images registered from different spatial directions can also ensue. In the case of examinations of the female breast, however, the spatial fixing thereof is a prerequisite for the signal calculation from different spatial directions.

The implementation of the invention is not limited to the preferred exemplary embodiment recited above. Numerous modifications are conceivable that make use of the illustrated solution even given fundamentally differently constituted embodiments.

Although modifications and changes may be suggested by those skilled in the art, it is the intention of the inventors to embody within the patent warranted hereon all changes and modifications as reasonably and properly come within the scope of their contribution to the art.

I claim:

1. A method for examining a body portion of a human subject, said body portion having a first ultrasound reflectivity associated therewith, said method comprising the steps of:

clamping and spatially fixing said body portion between a plate element and a reference surface parallel to said plate element, said reference surface having a second ultrasound reflectivity associated therewith which is higher than said first ultrasound reflectivity and said plate element being ultrasound transparent;

emitting ultrasound signals into said body portion along an axis perpendicular to said reference surface, said ultrasound signals proceeding through said plate element and said body portion to said reference surface and said body portion and said reference surface thereby producing respective ultrasound echo signals, each of said ultrasound echo signals having echo signal parameters associated therewith comprising a transit time along said axis and an amplitude;

receiving said echo signals;

identifying at least one reference parameter comprising at least one of said echo signal parameters for a reference echo signal passing through said body portion and reflected from said reference surface;

identifying at least one of said echo signal parameters for each echo signal upon reception of the respective echo signals;

identifying a deviation from said at least one reference parameter of the at least one echo signal parameter identified for each signal upon reception of the echo signal; and identifying a probability of the presence of a tumor in said body portion dependent on said deviation.

2. A method as claimed in claim 1 wherein the step of identifying a deviation from said at least one reference parameter comprises calculating a reduction of said at least one echo signal parameter identified for each echo signal upon reception of the echo signal relative to said at least one reference parameter.

3. A method as claimed in claim 1 wherein the step of identifying a deviation from said at least one reference parameter comprises the steps of:

selecting said amplitude as said at least one echo signal parameter and as said at least one reference parameter;

setting an amplitude threshold;

setting a time window; and identifying as said deviation any amplitude of each echo signal which exceeds said threshold during said time window.

4. A method as claimed in claim 3 comprising the additional step of storing said deviation.

5. A method as claimed in claim 4 comprising the additional steps of:

obtaining further ultrasound echoes from said body portion, said further ultrasound echoes each having an amplitude; and augmenting said further ultrasound echoes with the deviations stored in said memory and logically combining said deviations stored in said memory with said amplitudes of said further ultrasound echoes.

6. A method as claimed in claim 1 wherein the step of emitting ultrasound signals into said body portion comprises emitting ultrasound signals into said body portion successively along respective axes perpendicular to said reference surface, said axes being substantially equidistantly spaced apart.

7. A method as claimed in claim 6 comprising the additional step of superimposing echo signals obtained from each of said successive axes for producing a common, three-dimensional display of said body portion.

8. A method as claimed in claim 1 wherein the step of identifying at least one reference parameter comprises designating an average value of at least one of said echo signal parameters for a plurality of said echo signals as said reference parameter.

9. A method as claimed in claim 1 wherein the step of identifying at least one reference parameter comprises selecting a predetermined value of at least one of said echo signal parameters and defining said predetermined value as said at least one reference parameter.

10. An apparatus for examining a body portion of a human subject, said body portion having a first ultrasound reflectivity associated therewith, said apparatus comprising:

an ultrasound transparent plate element;

a reference surface having a second ultrasound reflectivity associated therewith which is higher than said first ultrasound reflectivity;

means for clamping and spatially fixing said body portion between said plate element and said reference surface with said plate element and said reference surface being parallel;

emitting ultrasound signals into said body portion along an axis perpendicular to said reference surface for causing said ultrasound signals to proceed through said plate element and said body portion to said reference surface and said body portion and said reference surface thereby producing respective ultrasound signals, each of said echo signals having echo signal parameters associated therewith comprising a transit time along said axis and an amplitude;

means for receiving said echo signals;

means for identifying at least one reference parameter comprising one of said echo signal parameters for an echo signal passing through said body portion and reflected from said reference surface;

means for identifying at least one of said echo signal parameters for each echo signal upon reception of the respective echo signals;

means for identifying a deviation from said at least one reference parameter of the at least one echo signal parameter identified for each echo signal upon reception of the echo signal; and means for assigning a probability of the presence of a tumor in said body portion dependent on said deviation.

11. An apparatus as claimed in claim 10 wherein said means for emitting ultrasound signals and said means for receiving said echo signals comprise an ultrasound transducer array contained in said plate element.

12. An apparatus as claimed in claim 10 wherein said means for clamping and spatially fixing said body portion between said plate element and said reference surface comprise means for displaceably connecting said plate element and said reference surface relative to each other along said axis for selectively adjusting a distance between said reference surface and said plate element.

13. An apparatus as claimed in claim 10 further comprising a flexible, ultrasound transparent container containing an acoustic coupling medium, said container being clamped and spatially fixed together with said body portion between said plate element and said reference surface by said means for clamping and spatially fixing said body portion.

14. An apparatus as claimed in claim 13 wherein said coupling medium comprises material having a speed of sound therein substantially equal to a speed of sound in said body portion.

15. An apparatus as claimed in claim 13 wherein said coupling medium comprises material having an acoustic absorption substantially equal to an acoustic absorption of said body portion.

16. An apparatus as claimed in claim 10 further comprising means for moving said means for emitting ultrasound signals along a predetermined path for scanning a planar surface of said body portion.

17. An apparatus as claimed in claim 16 further comprising means for locking said means for emitting ultrasound signals at a selected position for emitting ultrasound signals into said body portion along said axis perpendicular to said reference surface.

18. An apparatus as claimed in claim 16 further comprising means for generating a signal identifying a position of said means for emitting ultrasound signals along said predetermined path.

19. An apparatus as claimed in claim 18 further comprising stepping motor means for moving said carriage on said means for clamping and spatially fixing along said direction parallel to said reference surface.

20. An apparatus as claimed in claim 10 further comprising a carriage, on which said means for emitting ultrasound signals is mounted, said carriage being movably mounted on said means for clamping and spatially fixing for movement in a direction parallel to said reference surface.

21. An apparatus as claimed in claim 20 further comprising means for locking said carriage in a selected position on said means for clamping and spatially fixing for emitting ultrasound signals into said body portion along said axis perpendicular to said reference surface.

22. An apparatus as claimed in claim 10 wherein said plate element has a concave surface and wherein said reference surface is concave, and wherein said means for clamping and spatially fixing said body portion comprises means for holding said plate element and said concave reference surface with said concave surface of said plate element facing said concave reference surface.

* * * * *